United States Patent [19]

Seubert et al.

[11] Patent Number: 4,921,840

[45] Date of Patent: May 1, 1990

[54] METHOD FOR THE PREPARATION OF LOW MOLECULAR WEIGHT ALKALI METAL HUMINATES

[75] Inventors: Bernhard Seubert, Edingen-Neckarhausen; Helmut Beilharz, Schriesheim; Werner Fickert, Mannheim; Gunter Jeromin, Heidelberg; Ulrich Spitaler, Freinsheim, all of Fed. Rep. of Germany

[73] Assignee: Rutgerswerke AG, Fed. Rep. of Germany

[21] Appl. No.: 162,802

[22] Filed: Mar. 1, 1988

[30] Foreign Application Priority Data

Mar. 12, 1987 [DE] Fed. Rep. of Germany ....... 3707910

[51] Int. Cl.$^5$ .............................................. A61K 31/70
[52] U.S. Cl. ....................................................... 514/33
[58] Field of Search ........................................... 514/33

[56] References Cited

PUBLICATIONS

Lindquist et al.—Lantbr. Högsk Annaler, vol. 35, 815–822 (Sweden) 1969.

Primary Examiner—Leonard Schenkman
Attorney, Agent, or Firm—Bierman & Muserlian

[57] ABSTRACT

The invention relates to a synthetic preparation of alkali metal salts of low molecular weight humic acids wherein multi-valent phenols are oxidized in a weakly alkaline aqueous medium at a temperature in the range of 15° to 40° C. Subsequently, the reaction mixture is adjusted to a pH value ranging between 6.2 and 7.2 and/or buffered. The low molecular alkali metal huminate is then purified through purification means including preparatory chromotography, ultra-filtration, ultra-centrifugation, or electrodialysis and separated from undesirable by-products.

13 Claims, No Drawings

METHOD FOR THE PREPARATION OF LOW MOLECULAR WEIGHT ALKALI METAL HUMINATES

STATE OF THE ART

The invention relates to the synthetic preparation of alkali metal salts of low molecular weight humic acids. It has been found that low molecular weight alkali metal salts of humic acids have therapeutic properties, and in contrast to known humic matter are considerably less toxic. Low molecular weight humic matter, the object of a parallel application of the Applicant is indeed present as a fraction within the spectrum of naturally occurring humic matter. However, this fraction is found in relatively small quantities, and the isolation thereof is very expensive and time consuming.

Ziechmann, Huminstoffe (Humic Matter), (publ. Chemie 1980) describes a process wherein products similar to humic matter can be obtained. This process requires the oxidation of phenols, preferentially multi-valent phenols. These products however, in many respects differ from the naturally occurring humic matter.

OBJECTS OF THE INVENTION

It is therefore an object of the invention to make available a simple, synthetic method whereby low molecular humic acids are obtained with high yield and without great expenditures. These low molecular weight humic acids can be isolated as alkali metal salts and used as therapeutic agents.

This and other objects and advantages of the invention will become obvious from the following detailed description.

THE INVENTION

It has been found that low molecular weight alkali metal salts of humic acids have therapeutic properties, and in contrast to known humic matter, are considerably less toxic. It has now been found that under specific alkaline conditions through the oxidation of multi-valent phenol, low molecular weight alkali metal huminates can be prepared which substantially correspond to the naturally occurring low molecular weight alkali metal huminates, primarily with respect to their therapeutic effect and low level of toxicity.

In a synthetic preparation thereof, it has been surprisingly found that under the chosen conditions, the multi-valent phenols react quantitatively and the conversion does not lead to high molecular products. Instead, the reaction automatically reaches completion with a product with a mean molecular weight of approximately 1,000, the molecular weights ranging between 300 and 1,500 and therefore, are classed in the category of low molecular humic matter.

Starting materials for the method of the invention include all common multi-valent phenols, including catechol, resorcin, hydroquinone, orcin, gallic acid, protocatechuic, pyrogallol, 2-oxyhydroquinone, phloroglucinol, or tetraoxybenzole. The multi-valent phenols can be used as pure substances or in any mixture. The preferred multi-valent phenol is hydroquinone.

In the process, multi-valent phenols are dissolved in an aqueous alkali solution. As alkali solutions, all alkali metal hydroxides can be used. For cost efficiency, sodium and potassium hydroxide are preferred. The quantity of alkali metal hydroxide must be between 1.4 and 1.6 times the stoichiometric amount of phenols. This amount is required for the phenolate formation of the multi-valent phenols, or in other words, the neutralization of all phenolic OH groups. The pH value of the reaction solution should be maintained between 8.8 and 9.

The utilized compounds should be as pure as possible in order to avoid undesirable side reactions. Further, the use of pure compounds will result in final products that can be obtained without further chemical processing and which would lack undesirable chemical changes of the end product. Water used in the reaction should be demineralized with a conductivity of 6 to 10 uS/cm and a pH value ranging from 5 to 7. Alkali metal hydroxide used should be of "chemically pure" quality or the purification grade of DAB 8. The multi-valent phenol likewise should be of "chemically pure" quality and should have a content of multi-valent phenols of more than 98%.

The oxidation of a multi-valent phenolate can take place either electro-chemically or plasma-chemically by guiding oxygen or an oxygen containing gas mixture through or over the material. Electro-chemical oxidation is carried out in an electro-chemical reactor, with the oxidation rate being determined by setting the anode voltage and the current density. The anode voltage can be varied in the range of 4 to 15 V and the current density in the range of 0.5 to 4 $A/cm^2$. The reaction time ranges from 1 to 3 days.

The plasma-chemical oxidation takes place in an apparatus for corona discharge with the oxidation rate being determined by setting the operating voltage and field strength. The voltage can be varied in a range from 20 to 250 KV at frequencies from 16 2/3 to 400 Hz and the field strength from 80 KV/cm to 200 KV/cm. The reaction time here would range from 15 to 120 minutes.

For chemical oxidation, the alkali solution of the multi-valent phenolate is placed in a reaction vessel which prevents uncontrolled access by air. While being stirred, oxygen or an oxygen-containing gas mixture is guided either over or through the reaction solution or is guided under pressure into the reaction solution with the temperature of the reaction mixture being maintained in the range of 10° to 40° C., preferentially at a room temperature of up to 30° C.

Air can be used as the oxygen-containing gas. However, the air must previously have been guided through an alkaline filter to absorb $CO_2$ and to remove dust particles. The oxidation reaction lasts, depending on the temperature and intensity of the oxygen supply selected, from 5 to 20 days. During this reaction time, the solution turns intensely dark brown. The chemical oxidation can also take place through reaction with mild oxidation reagents including hydrogen peroxide, its addition compounds, or persulfates.

It is an advantage of the process of the invention that under the reaction conditions selected as well as with the electrochemical or plasma chemical oxidation as well as with the chemical oxidation, the formation of the humic matter does not lead to high molecular weight products. Instead, the reaction will come to a stand still on its own with products having an average molecular weight of 1,000, the individual molecular weights being within a range of 300 to 1,500. This obviates continuous surveillance throughout the course of the oxidation reaction and reaction time may be longer without adverse consequences.

After oxidation, the dark brown solution is neutralized, adjusted to a pH value ranging from 6.2 to 7.2, preferentially, 6.6 and buffered. This takes place either through the addition of acid, or by the use of an acidic ion exchanger and/or subsequent addition of an appropriate buffer solution, (for example, phosphate-, tris- or citric acid).

If the neutralized and buffered solution contains unwanted suspended matter, this matter can now be removed through a separation process, including centrifugation, (10,000 to 30,0000 xg), or filtration through a very fine pored filtering material. Although this solution can be used for many applications immediately, when these products are used for medicinal purposes, they should be purified in purification processes such as preparatory chromotography, ultra-filtration, ultra-centrifugation or electrodialysis to further free the solution of unwanted by-products.

The obtained solution contains approximately 3 to 5% low molecular alkali metal huminates. This solution can be used directly or it can be concentrated to a 20% solution, possibly by lyophilizing. The obtained concentrated solutions are stable.

After sixty days of stability testing during which an alternating 56/4° C. stress was introduced every twelve hours, there were no changes in the parameters content, pH value, oxidation/reduction potential, or microdialysis that could be detected beyond random deviations. Toxicity tests show that the obtained low molecular alkali metal huminates have therapeutic properties like those observed with the naturally occurring low molecular weight humic matter, in particular, in the area of wound healing. The low molecular alkali metal huminates according to the invention are therefor suitable as therapeutic agents, in particular, as therapeutic agents in wound healing.

Due to the synthetic preparation of the alkali metal huminates, fluctuations of composition and molecular structure, as they occur during the natural course of the humification process, can be greatly reduced. The low molecular alkali metal huminates according to the invention, therefore, are more uniform than the corresponding natural products and are extremely well suited for preparing standardized therapeutic agents. They are especially suited for the standardization of strongly fluctuating natural products like moor baths or mud baths. The synthetically prepared low molecular weight alkali metal huminates can be used as highly effective moor bath substitutes, or they can be added to natural moor baths.

In the following examples, there are described several preferred embodiments to illustrate the invention. However, it should be understood that the invention is not intended to be limited to the specific embodiments.

EXAMPLES

In an alkali resistant agitator 3.2 kg of sodium hydroxide (50%, DAB 8) were mixed with 100 l of demineralized water (pH 5 to 7; conductivity less than 5 $\mu X$/cm). At a temperature range between 20° and 30° C. in the course of 45 minutes, 5 kg hydroquinone (chemically pure, above 99%) were added. The apparatus was closed and then air, which was purified through an alkaline filtering system from dust, $CO_2$ and other contaminants, was conducted over the surface. Stirring took place over 14 days with an interval circuit being used, which sets the agitator in motion every 15 minutes for 3 to 5 minutes. Through the absorption of oxygen from the air, the solution turned intensely dark brown in time. The reaction temperature was in the range of 20° to 25° C.

By adding ortho-phosphoric acid, the solution was then adjusted to pH 6.6 and simultaneously buffered. Through prefiltration through a fine pored filter (20 to 40 $\mu$m), suspended matter was kept from the dialysis equipment. From this solution, the alkali metal huminates according to the invention were obtained as brown solution in an electrodialysis device, which was equipped with a membrane of 0.025 $\mu$m of sintered glass, by applying a direct voltage of 200 V.

The dialysis residue was continuously pumped in order to avoid concentration polarization. The following values were checked while the dialysis was in progress:

| pH value | 6.4 to 6.8 |
|---|---|
| Microdialysis test | negative |

On the basis of the electrophoretic migration rate, an average molecular weight for the so prepared huminate of 1,000 was determined with a spread of 300 to 1,500.

Toxicity: following injections of the 1% solution into test animals (mice), the following values of the $LD_{50}$ were obtained:

| subcutaneous | 1250 (mg/kg) |
|---|---|
| intraperitoneal | 810 |
| intravenous | 770 |

Stability:

After 6 months storage under exclusion of air at 23° C., no changes were detected.

Therapeutic effect:

A culture of L-cells (mouse fibroblasts) brought into suspension after treatment with trypsin was mixed with 50 ppm low-molecular weight alkali metal huminate. The culture was incubated for 48 hours at 37° C. using a commercially available nutrient medium.

Parallel to this as a control test, an analog culture without alkali metal huminates was likewise incubated. Subsequently, the number of viable cells in both cultures was determined. In the culture mixed with the low-molecular weight alkali metal huminates, the number of viable cells was approximately 30% greater than in the control culture.

Wound healing:

Superficial wounds involving only the uppermost epithelial layers approximately 50 mm² large were inflicted on 2×10 hairless mice. In ten of these mice, the wound was wetted once with a 1% solution. The other mice remained untreated. During the observation time of 7 days, the following can be observed: Compared to the untreated mice in the treated test animals the area of the wound decreased more rapidly, the wound dried sooner, granulation started earlier, and the wound became clean sooner. Overall, healing was observed 2 to 3 days earlier than in the control animals.

Various modifications of the process of the invention may be made without departing from the spirit or scope thereof and it should be understood that the invention is to be limited only as defined in the appended claims.

What is claim is:

1. A method of preparing low molecular weight alkali metal huminates wherein a reaction mixture comprising multi-valent phenols in a weak alkali metal aqueous medium are oxidized at a pH range from 8.8 to 9 and at a temperature ranging from 15° to 40° C., said reaction mixture is adjusted to a pH value ranging from 6.2 to 7.2 and/or buffered, the low molecular weight alkali metal huminates are purified, and undesirable by-products are separated therefrom.

2. The method of claim 1 wherein the alkali metal aqueous medium is present in a stoichiometric quantity 1.4 to 1.6 times that of the multi-valent phenol.

3. The method of claim 1 wherein the multi-valent phenol is hydroquinone.

4. The method of claim 1 wherein the oxidation takes place by treatment with oxygen or an oxygen-containing gas.

5. The method of claim 1 wherein the oxidation takes place electro-chemically.

6. The method of claim 1 wherein the oxidiation takes place plasma-chemically.

7. The method of claim 1 wherein the oxidation takes place using mild oxidation agents.

8. The low molecular weight alkali metal huminates prepared according to the method of claim 1.

9. The method of claim 1 wherein purification is by ultra-centrifugation.

10. The method of claim 1 wherein purification is by electrodialysis.

11. The method of claim 1 wherein purification is by ultra-filtration.

12. The method of claim 1 wherein purification is by preparatory chromotography.

13. A method of increasing the healing rate of a wound in warm-blooded animals comprising applying to a wound of a warm-blooded animal, an amount of an alkali metal huminate prepared by the process of claim 1 sufficient to increase the healing rate.

* * * * *